(12) United States Patent
Carnell et al.

(10) Patent No.: US 11,298,526 B2
(45) Date of Patent: *Apr. 12, 2022

(54) DEVICE FOR HEALING WOUNDS

(71) Applicant: UNITED STATES OF AMERICA AS REPRESENTED BY THE ADMINISTRATOR OF NASA, Washington, DC (US)

(72) Inventors: Lisa S. Carnell, Virginia Beach, VA (US); Emilie J. Siochi, Newport News, VA (US); Kam W. Leong, New York, NY (US)

(73) Assignee: UNITED STATES OF AMERICA AS REPRESENTED BY THE ADMINISTRATOR OF NASA, Washington, DC (US)

( * ) Notice: Subject to any disclaimer, the term of this patent is extended or adjusted under 35 U.S.C. 154(b) by 280 days.

This patent is subject to a terminal disclaimer.

(21) Appl. No.: 16/564,987

(22) Filed: Sep. 9, 2019

(65) Prior Publication Data
US 2019/0388677 A1 Dec. 26, 2019

Related U.S. Application Data

(63) Continuation of application No. 12/699,334, filed on Feb. 3, 2010, now Pat. No. 10,406,346.
(Continued)

(51) Int. Cl.
*A61N 1/04* (2006.01)
*A61F 13/00* (2006.01)
(Continued)

(52) U.S. Cl.
CPC ...... *A61N 1/0468* (2013.01); *A61F 13/00051* (2013.01); *A61F 13/023* (2013.01);
(Continued)

(58) Field of Classification Search
CPC .... A61N 1/0468; A61N 1/205; A61N 1/0464; A61N 1/0492; A61F 13/00051;
(Continued)

(56) References Cited

U.S. PATENT DOCUMENTS 5,030,255 A 7/1991 Aebischer
5,109,861 A 5/1992 Walinsky et al.
(Continued)

OTHER PUBLICATIONS

Y. Bar-Cohen "Electroactive polymers as artificial muscles reality and challenges." Proceedings of the 4th Aerospace Materials, Processes, and Environmental Technology (AMPET) Conference, Huntsville, AL. Sep. 19, 2000, 10 pages.
(Continued)

*Primary Examiner* — Tammie K Marlen
(74) *Attorney, Agent, or Firm* — Robin W. Edwards; Jennifer L Riley; Helen M. Galus

(57) ABSTRACT

A device for promoting healing of an injury in a living being is provided. Such device is based upon an injury covering portion, which portion comprises an electroactive polymer, such as poled polyvinylidine difluoride (PVDF) or a copolymer of PVDF. The electroactive polymer has either pyroelectric properties, piezoelectric properties, or both.

6 Claims, 3 Drawing Sheets

Related U.S. Application Data

(60) Provisional application No. 61/151,532, filed on Feb. 11, 2009.

(51) Int. Cl.
  *A61F 13/02* (2006.01)
  *A61L 15/24* (2006.01)
  *A61L 15/42* (2006.01)
  *A61N 1/20* (2006.01)

(52) U.S. Cl.
  CPC .............. *A61L 15/24* (2013.01); *A61L 15/42* (2013.01); *A61N 1/205* (2013.01); *A61F 2013/00936* (2013.01); *A61N 1/0464* (2013.01); *A61N 1/0492* (2013.01)

(58) Field of Classification Search
  CPC ......... A61F 13/023; A61F 2013/00936; A61L 15/24; A61L 15/42
  See application file for complete search history.

(56) References Cited

U.S. PATENT DOCUMENTS

| | | | |
|---|---|---|---|
| 5,219,659 A | 6/1993 | Weber | |
| 5,240,004 A | 8/1993 | Walinsky | |
| 5,910,458 A | 6/1999 | Beer et al. | |
| 5,964,783 A | 10/1999 | Grafton et al. | |
| 6,309,550 B1 | 10/2001 | Iversen et al. | |
| 6,582,383 B2 | 6/2003 | Horning | |
| 2001/0055622 A1 | 12/2001 | Burrell et al. | |
| 2002/0011300 A1* | 1/2002 | Cass | B29C 70/20 156/89.12 |
| 2005/0245857 A1 | 11/2005 | Pizzi et al. | |
| 2006/0018954 A1 | 1/2006 | Kuttler | |
| 2006/0057377 A1* | 3/2006 | Harrison | H01L 41/193 428/364 |
| 2006/0129216 A1 | 6/2006 | Hastings et al. | |
| 2007/0100274 A1 | 5/2007 | Young et al. | |
| 2007/0257634 A1 | 11/2007 | Leschin et al. | |
| 2008/0004564 A1* | 1/2008 | Smith | A61N 1/303 604/20 |
| 2013/0115839 A1 | 5/2013 | Arvidson et al. | |

OTHER PUBLICATIONS

Carnell, et al., "Delivering Electrical and Mechanical Stimuli through Bioactive Fibers for Stem Cell Tissue Engineering", Thesis Proposal—Duke University, 21 pages.

Website, http://www.chm.bris.ac.uk/webprojects2004/phillips/PZ/pz-pollng.html, Bristol University, 2004.

* cited by examiner

DEVICE FOR HEALING WOUNDS

ORIGIN OF THE INVENTION

This patent application is a continuation of and claims the benefit of priority to U.S. Non-Provisional patent application Ser. No. 12/699,334 filed on Feb. 3, 2010, now U.S. Pat. No. 10,406,346 B2, which claims the benefit of U.S. Provisional Application No. 61/151,532, filed Feb. 11, 2009.

The invention was made by employees of the United States Government and may be manufactured and used by or for the Government of the United States of America for governmental purposes without the payment of any royalties thereon or therefor.

FIELD OF THE INVENTION

The present invention relates generally to devices for wound healing, and specifically to devices for healing wounds by the application of electrical stimulation.

BACKGROUND

Although the United States spends nearly $20 billion annually to care for individuals suffering from chronic wounds, chronic wound care is still considered a grand challenge by the National Institutes of Health. Solutions to expedite wound healing would result in substantial savings and enhance the quality of life, particularly for individuals suffering from persistent diabetic ulcers. Just as efficient and effective wound care is desirable in terrestrial applications, improved wound healing is also a concern in astronaut health care.

Innovative approaches such as bioinspiration, i.e., mimicking how the body heals itself, have spawned various wound healing technologies. For example, there are novel materials and techniques based on delivering biological chemicals such as growth factors to a wound site. The results from these approaches have been promising at minimizing scar tissue, but accelerated wound healing has not been demonstrated. Other methods that have been tried include application of light emitting diodes, ultrasound and near infrared laser exposure. However, these techniques have not proven practical for general public use.

Electrical stimulation at the wound site is a new avenue that has been moderately explored since the early 1980s. Electric fields have been demonstrated to play a critical role in controlling the migration of cells to the wound site following injury. Based on this premise, several products designed to expedite the wound healing process through the application of electric fields have been introduced commercially. However, prior art devices for applying electric fields to wound sites rely on AC or DC power to generate the electric fields. As a result, such devices are cumbersome, complex and expensive, thereby limiting their use.

BRIEF SUMMARY

Embodiments of the invention provide simple, lightweight approaches for generating electrical stimulation at the wound site. Embodiments of the invention have potential to be implemented in a simple, lightweight package suitable for patient care in many different settings, such as hospital, clinic, home, military, emergency medical services, and even space missions. Additional benefits anticipated include bacterial resistance and the potential for recyclability.

In one embodiment of the invention, a device for promoting healing of an injury in a living being (such as a human being or other animal) comprises an injury covering portion. The device may further comprise an adhering portion. The injury covering portion comprises an electroactive polymer, such as poled polyvinylidine difluoride (PVDF) or a copolymer of PVDF. The electroactive polymer has either pyroelectric properties, piezoelectric properties, or both. The adhering portion adheres the device to a living being.

The injury covering portion is sized to at least partially cover the injury. The injury covering portion advantageously comprises one of an electroactive polymer film, a perforated electroactive polymer film, a woven electroactive polymer fiber, or a non-woven electroactive polymer fiber. Examples of possible electroactive polymer films, and methods for their preparation can be found in co-pending U.S. patent application Ser. No. 12/131,420, filed Jun. 2, 2008 by Scott-Carnell, et al., entitled "Method and System for Aligning Fibers During Electrospinning" now issued as U.S. Pat. No. 7,993,567 B2; and co-pending U.S. patent application Ser. No. 12/274,652, filed Nov. 20, 2008, by Wincheski, entitled "Method for Predicting and Optimizing System Parameters for Electrospinning System," now issued as U.S. Pat. No. 7,901,611 B2, which applications are hereby incorporated by reference as if set forth in their entirety. The injury covering portion may comprise a coating on at least one surface of the injury covering portion. The coating may comprise one of a biodegradable polymer or a precious metal.

The device may further comprise a heat source for applying heat to the injury covering portion, such as an external heat source.

BRIEF DESCRIPTION OF THE SEVERAL VIEWS OF THE DRAWINGS

Figure 1:
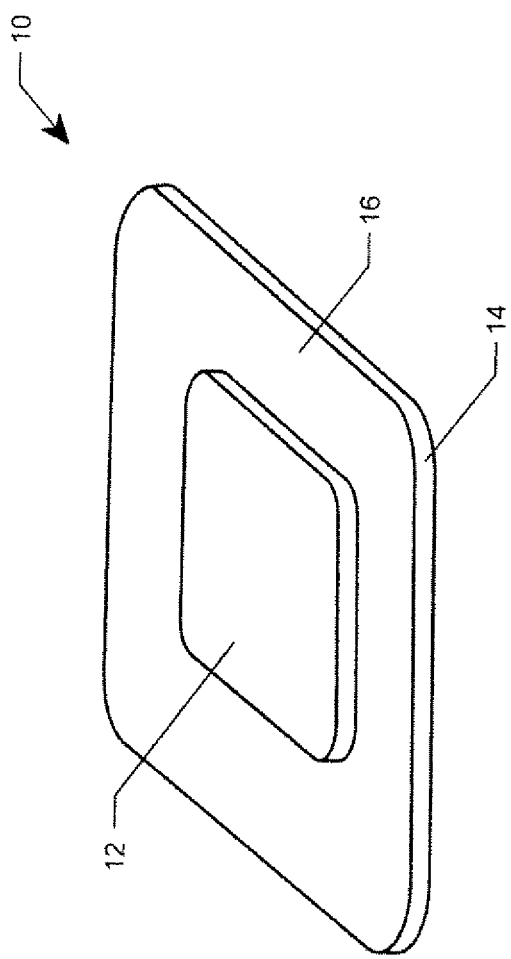
Figure 2:
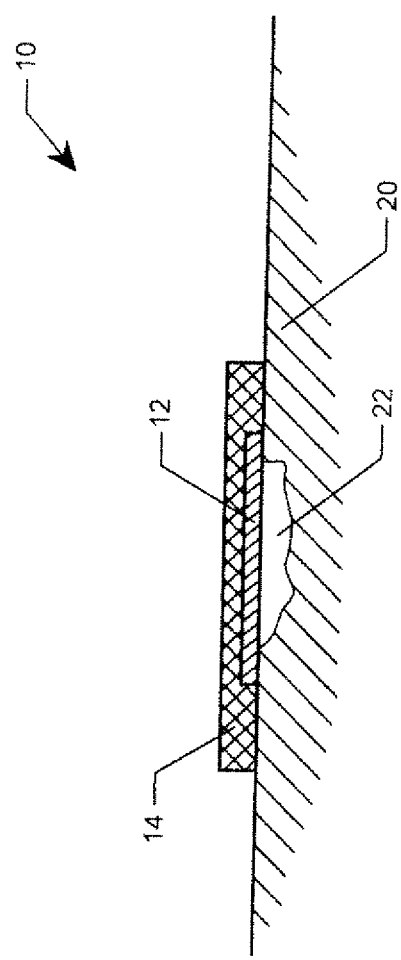
Figure 3:
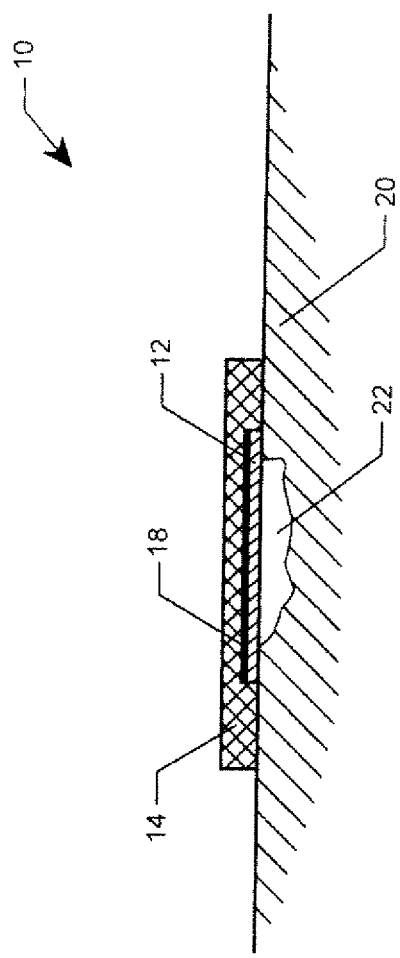

Having thus described the invention in general terms, reference will now be made to the accompanying drawings, which are not necessarily drawn to scale, and wherein:

FIG. 1 is a perspective view of a device for promoting healing of an injury, in accordance with embodiments of the present invention;

FIG. 2 is a cross-sectional view of the device of FIG. 1 applied to an injury; and FIG. 3 is a cross-sectional view of a device similar to the device shown in FIG. 2 but with the addition of a coating, in accordance with embodiments of the present invention.

DETAILED DESCRIPTION

Embodiments of the invention utilize an electroactive polymer, such as polyvinylidene fluoride (PVDF) or a copolymer of PVDF, to promote and accelerate healing of an injury. The electroactive polymer may be incorporated into a bandage or used as a gauze pad to cover a wound and to facilitate the wound healing process. Alternatively, the electroactive polymer may be used as a suture material to suture a wound and to facilitate the wound healing process. The novelty of this technology lies in the ability to influence cell migration at the wound site through the application of an electric field generated by the inherent pyroelectric and piezoelectric properties of electroactive polymers, such as electroactive PVDF and copolymers thereof. Lab studies have shown intrinsic electroactivity is present when an electroactive polymer such as PVDF is exposed to 37° C. without the need to apply voltage. Specifically, a slight charge of 0.28 nanoamps is emitted at 37° C. (normal human body temperature) as measured using thermally stimulated current methods on electroactive PVDF film. Thus, based on previous research with electric fields, embodiments of the invention should expedite the wound healing process significantly. As 37° C. is normal human body temperature, when applied to a human body embodiments of the invention exhibit intrinsic electroactivity from the body heat without the need for an external heat source.

While any suitable electroactive polymer may be used (e.g., PVDF, co-polymers PVDF-TrFE, etc.), embodiments of the invention will be described herein as using PVDF as the electroactive polymer. In vitro studies have shown PVDF to be biocompatible. In addition to the electroactivity caused by the application of heat, the piezoelectricity in PVDF manifests itself as the generation of voltage with application of pressure. For example, the pressure exerted by cell growth or tissue swelling during healing may be sufficient to induce an electric field in the PVDF due to its piezoelectricity. Thus, two separate properties of PVDF (its inherent pyroelectric properties and its inherent piezoelectric properties) work together to induce an electric field in the PVDF.

PVDF is rendered electroactive by the processing method employed in manufacturing. Through this process, multi-layer meshes can be fabricated with semi-controlled porosities to allow oxygen penetration while maintaining moisture resistance. The electroactive nature of the material serves as a barrier to most bacteria and viruses due to their polar characteristics, providing an additional intrinsic benefit. The fibers may have a diameter from 0.5 to 18 µm. The fibers may be electrospun using an elliptical electric field formed by a dispenser and an electrode to orient the plurality of aligned, non-woven electroactive polymer fibers on an uncharged collector. Multiple-ply fiber mats can be fabricated with fiber orientation between the plies being pre-determined. One method of accomplishing this is to attach a polymer film to the collector and deposit aligned fibers thereon as described in U.S. application Ser. No. 12/131,420 (incorporated by reference above). The resulting polymer film/fiber mat can be removed from the collector and then repositioned on the collector so that the next ply of aligned fibers are deposited on the first ply at a pre-determined orientation with respect thereto. This process can be repeated as frequently as desired until the desired mat thickness is achieved. For example, pseudo-woven mats having a plurality of single fibers or fiber bundles in each layer, with all fibers in a layer aligned with and substantially parallel to one another, were generated by electrospinning multiple layers in a 0°/90° lay-up to create a porous multi-ply mat. This was achieved by electrospinning the first layer onto a Kapton® film attached to the collector, removing the polymer film, rotating it 90°, reattaching it to the collector and electrospinning the second layer on top of the first, resulting in the second layer lying 90° relative to the first layer.

PVDF has been used in the biomedical industry in the non-polar form for decades. The biocompatibility of electroactive PVDF film was confirmed by a standard live/dead assay as well as in vitro stem cell culture assays performed over 14 day periods.

FIG. 1 is a perspective view of a device for promoting healing of an injury in accordance with embodiments of the present invention. FIG. 2 is a cross-sectional view of a device for promoting healing of an injury in accordance with embodiments of the present invention. In the embodiment illustrated in FIGS. 1 and 2, the device 10 is in the form of an adhesive bandage which comprises an injury covering portion 12 mounted on a substrate 14. The surface of the substrate surrounding the injury covering portion is coated with an adhesive and thereby comprises the adhering portion 16. As in a typical adhesive bandage, the device 10 would be applied to a human (or any other living animal if desired) such that injury covering portion is in contact with and covers the injury 22 and such that the adhering portion adheres to the skin 20 surrounding the injury to keep the device in place. Unlike a typical adhesive bandage, the injury covering portion comprises an electroactive polymer, such as poled polyvinylidine difluoride (PVDF). As discussed above, the pyroelectric properties and/or the piezoelectric properties of the electroactive polymer, when exposed to body heat and/or pressure, such as from cell growth, cause an electric field to be applied to the injury thus promoting healing. Embodiments of the invention may also reduce scarring and may reduce infection.

In addition to an adhesive bandage, embodiments of the invention could alternatively comprise a gauze-like pad without an adhering portion. In such an embodiment, a separate means of adhering the gauze-like pad to the skin would be used, such as adhesive tape or a standard gauze roll. As a further alternative, embodiments of the invention could comprise a suture material (i.e., a thread-like strand) made of electroactive polymer. Such a suture material would have the double advantage of mechanically closing a wound and promoting cell growth.

Embodiments of the invention may be constructed in any suitable size, to cover wounds of many different sizes. Embodiments of the invention may comprise an electroactive polymer film, a perforated electroactive polymer film, a woven electroactive polymer fiber, or a non-woven (aligned) electroactive polymer fiber. Embodiments of the invention may be processed as cast film, extruded as fiber, or electrospun. Embodiments of the invention may be post-processed, such as by stretching (axially or biaxially) or being subjected to an electric field to further induce poling.

As shown in FIG. 3, a coating 18 (such as a biodegradable polymer or a precious metal (silver or gold)) may be applied to at least one surface of the electroactive polymer 12. The metal coating may help increase heat retention and/or provide microbial resistance.

Embodiments of the invention could potentially be recycled (i.e., may be reusable if properly disinfected). A supplemental/external heat source (i.e., in addition to body heat) and/or pressure source (i.e., in addition to cellular growth, for example) may be applied to the electroactive polymer which may further reduce wound healing time. Embodiments of the invention may be applied directly to a wound or indirectly through another layer.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed as new and desired to be secured by Letters Patent of the United States is:

1. A device comprising: an injury covering portion configured to promote healing of an injury in a living being without the need to apply voltage during use and comprising a porous multilayer fiber mat comprising a plurality of layers, wherein each layer comprises a plurality of non-woven electroactive polymer fibers, wherein all of the fibers in a layer are aligned with and substantially parallel to one another, the fibers having both pyroelectric and piezoelectric properties, and the fibers comprising a poled polyvinylidine difluoride or a poled copolymer of polyvinylidine difluoride, wherein the fibers are electrospun.

2. The device of claim 1, further comprising: an adhering portion for adhering the device to a living being.

3. The device of claim 1, wherein the injury covering portion is sized to at least partially cover the injury.

4. The device of claim 1, wherein the injury covering portion comprises a coating on at least one surface of the injury covering portion.

5. The device of claim 4, wherein the coating comprises one of a biodegradable polymer or a precious metal.

6. The device of claim 1, further comprising: a heat source for applying heat to the injury covering portion.

* * * * *